United States Patent [19]
Freitas et al.

[11] Patent Number: 5,472,451
[45] Date of Patent: Dec. 5, 1995

[54] ENDOSCOPIC SURGICAL INSTRUMENT WITH ACUTE ANGLE ORIENTATION

[76] Inventors: Michael W. Freitas, 8421 Castle Creek, North Richard Hills, Tex. 76180; Troy J. Mullens, Jr., 3720 London La., North Richland Hills, Tex. 76118; Dale H. Brancel, 2700 Sherwood, Colleyville, Tex. 76034; Walter B. Herbst, 86 Salem La., Evanston, Ill. 60203; Paul Hurley, 812 W. 19th St., 2 Rear, Chicago, Ill. 60608; Thomasz Milewski, 4151 N. Overhill, Norridge, Ill. 60634; Kim Vollendorf, 24941 W. Forest Dr., Lake Villa, Ill. 60046; James F. Caruso, 1839 W. Lunt, Apt. 2, Chicago, Ill. 60626

[21] Appl. No.: 215,014

[22] Filed: Mar. 21, 1994

Related U.S. Application Data

[63] Continuation of Ser. No. 943,903, Sep. 11, 1992, abandoned.

[51] Int. Cl.⁶ ............................................. A61B 17/42
[52] U.S. Cl. ............................................. 606/205; 606/208
[58] Field of Search ............................ 606/205–209, 606/139, 144, 51–52, 174; 128/751

[56] References Cited

U.S. PATENT DOCUMENTS

| | | | |
|---|---|---|---|
| H1028 | 3/1992 | Falk et al. | 606/205 |
| 4,084,594 | 4/1978 | Mosior | 606/174 |
| 4,815,476 | 3/1989 | Clossick | 606/707 |
| 4,899,734 | 2/1990 | Gelley | 606/205 |
| 5,133,735 | 7/1992 | Slater et al. | 606/205 |
| 5,160,343 | 11/1992 | Brancel et al. | 606/205 |
| 5,196,023 | 3/1993 | Martin | 606/207 |
| 5,261,917 | 11/1993 | Hasson et al. | 606/208 |
| 5,308,358 | 5/1994 | Bond et al. | 606/207 |
| 5,314,445 | 5/1994 | Heidmueller et al. | 606/208 |
| 5,334,198 | 8/1994 | Hart et al. | 606/52 |

Primary Examiner—Stephen C. Pellegrino
Assistant Examiner—Michael Peffley

[57] ABSTRACT

An endoscopic surgical instrument is manually manipulatable by a surgical operator. In one embodiment, the instrument provides an alignment between a hand-held grip and a housing whereby an acute angle is formed at the point of intersection of the axis of the housing and the axis of the grip. In another embodiment, the instrument provides a hand-held grip which includes a pivot portion through which the thumb of the operator is received and which may be pivoted laterally in relation to the housing. In another embodiment, the instrument provides up to complete axial rotation of the housing relative to an instrument body housed therein to permit ease of orientation of the housing and/or body during surgery.

11 Claims, 4 Drawing Sheets

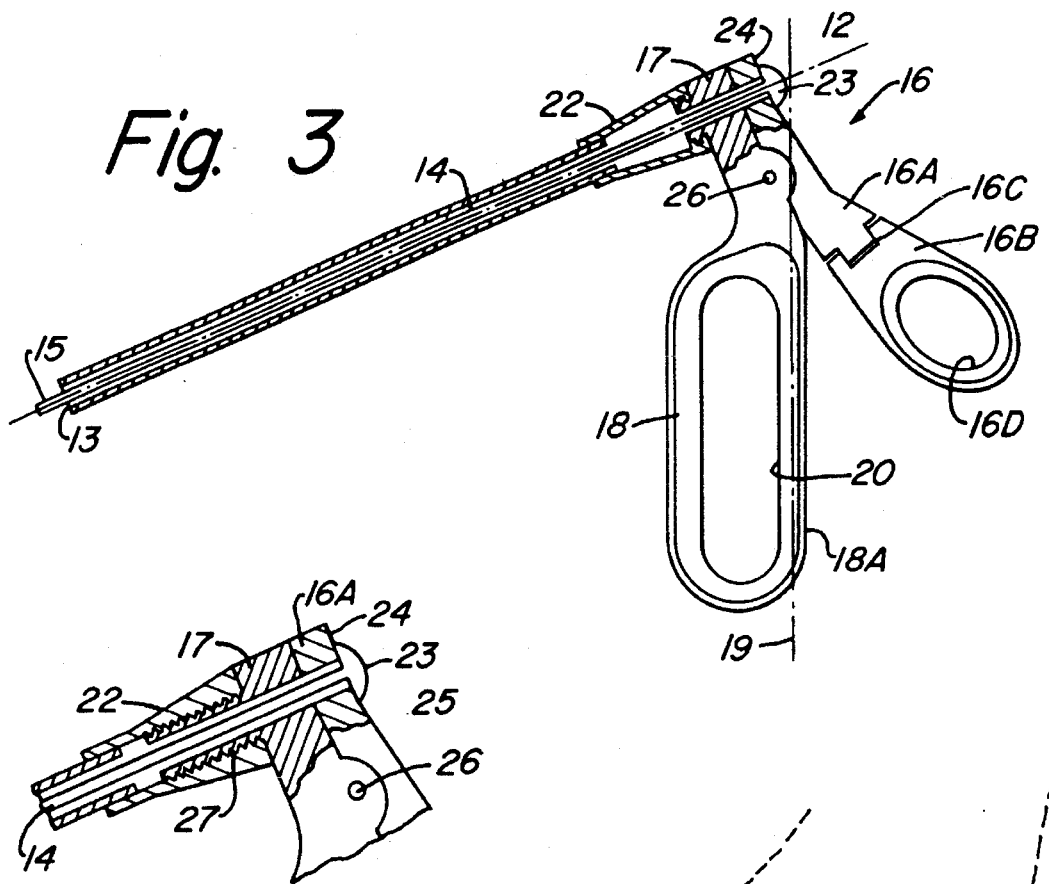
Fig. 3
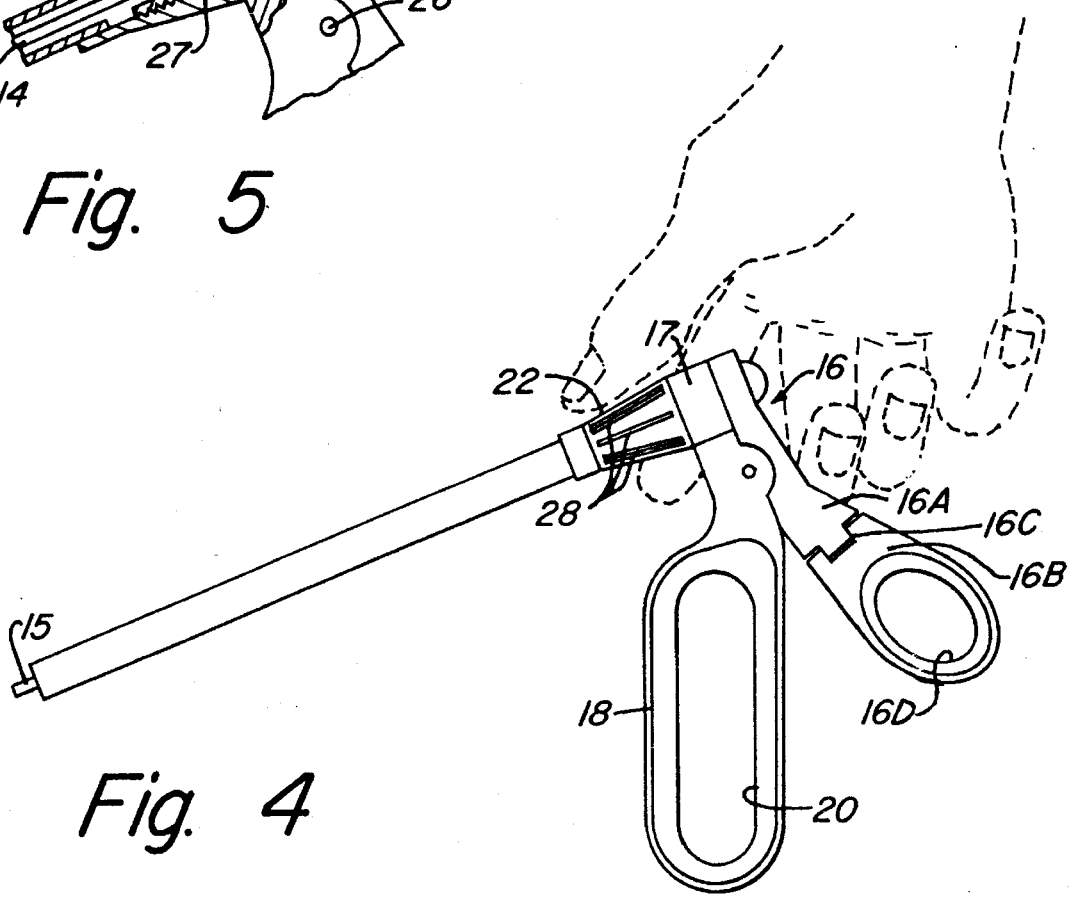
Fig. 5
Fig. 4

5,472,451

ENDOSCOPIC SURGICAL INSTRUMENT WITH ACUTE ANGLE ORIENTATION

This is a continuation of application Ser. No. 07/943,903, filed Sep. 11, 1992, now abandoned.

BACKGROUND OF THE INVENTION

1. Field of the Invention

The present invention relates to a endoscopic surgical instrument which may be manipulated by a human surgical operator, such as a doctor, nurse, or the like.

2. BRIEF DESCRIPTION OF THE PRIOR ART

Surgical procedures require considerable touch and feel of the surgeon in the operation of the particular surgical instrumentation in order to satisfactorily and carefully accomplish the desired objective of the surgical procedure. Accordingly, surgical instruments must incorporate into their design operability, the ability of the surgeon to rely on simply touch techniques for activation of the instruments. Additionally, such instruments should also be designed to avoid or reduce strain upon the arms, hands and fingers of the surgeon or other human surgical operator.

Such objectives are particularly critical with respect to endoscopic surgical instruments. Endoscopic procedures gain access to the inside of an anatomical cavity by using an implement, such as a trocar, cannula, or a needle having a sharpened point to pierce or puncture the bodily tissues, muscles, membranes, or the like, which may form a portion or surround the cavity wall. A surgical needle, for example, connected to a catheter may be used to pierce a cavity, a blood vessel, subarachnoid heat ventricle or the like. After piercing such cavity, the needle is left in situ and used to inject or withdraw gases or liquid-phase fluids from the cavity, or to insufflate the cavity by injection of, for example, a particular inert gas or other fluid, resulting in a laparoscopic environment.

Since the area in which the surgeon must perform procedures incorporating endoscopic surgical instrumentation is smaller than that normally encountered when conventional surgical techniques are employed, reliance by the surgeon upon touch and feel during the surgery becomes even more critical, and surgical instrumentation must take this factor into consideration such that touch and feel are transferred between the surgeon's hand and the fingers through the instrument and between the area of operation with the abdomen or other area and the surgeon's hand.

Many surgical instruments for use in endoscopic and conventional surgical procedures, such as forceps and other cutting instruments, incorporate a pistol-like handle. Typical of such prior art pistol-like handles is that as shown and described in U.S. Pat. No. 5,026,375, entitled "Surgical Cutting Instrument". Many such instruments include a protrusion or abutment on the pistol-like handle in order to receive the thumb of the surgeon. Accordingly, such instruments may not maximize surgical touch and feel between the area of surgery and the surgeon's hand.

In co-pending application Ser. No. 756,570, filed Sep. 9, 1991, and entitled "Surgical Instruments Handle & Forceps Assembly", assigned to the same assignee as the present application, there is shown and disclosed another type of endoscopic surgical instrument handle assembly.

The present invention addresses the problems and the deficiencies of the prior art, as discussed above.

SUMMARY OF THE INVENTION

An endoscopic surgical instrument which is manually manipulatable by a human surgical operator includes an elongated surgical instrument housing having a central axis and having a first end for introduction into the human body through a surgical incision, The surgical instrument body is disposed within the housing and is movable relative to the housing and has one end extendable through the first end of the instrument housing. Manipulator means are provided for controlling relative movements between the housing and the body. Control means are joined to the housing and have gripping means which include a grip axis for gripping the instrument by a plurality of fingers of a human surgical operator.

An acute angle is defined at the joinder of the housing and the control means between the axis of the housing and the grip axis such that the hand of the surgeon or other human operator when initially engaging the device emulates a relaxed position of the hand, thumb, fingers and wrist such that the hand, thumb and fingers and, in turn, the wrist and forearm of the surgeon or operator are essentially on a longitudinal axis of the gripping element and the fingers may move from a relaxed orientation thereon to secure the device during operation.

In one embodiment, the gripping means may have an entry through which the fingers of the surgical operator penetrate to encircle at least a portion of the gripping means for engagement. Means are provided for rotatably securing the housing to the control means whereby the housing at the first end may be selectively rotated up to 360 degrees around said instrument body for selective orientation of the housing and the instrument body before, during or after surgical proceedings.

In one embodiment, the manipulator means may include a finger activated pivot which is operatively connected to the instrument body and which is moveable between a neutral position to at least one of first and second positions to move the instrument body relative to the housing and between one of expanded and retracted positions.

BRIEF DESCRIPTION OF THE DRAWINGS

FIG. 3 is a view similar to that of FIG. 1, illustrating the instrument in partial section to show the relationship of the instrument body and housing members.

FIG. 4 is a view of the instrument similar to that shown in FIGS. 1 and 3, showing the hand of the operator manipulating a rotation means on the housing.

FIG. 5 is an enlarged sectional view of the housing, rotatable means and control member.

DESCRIPTION OF THE PREFERRED EMBODIMENT

Figure 1:
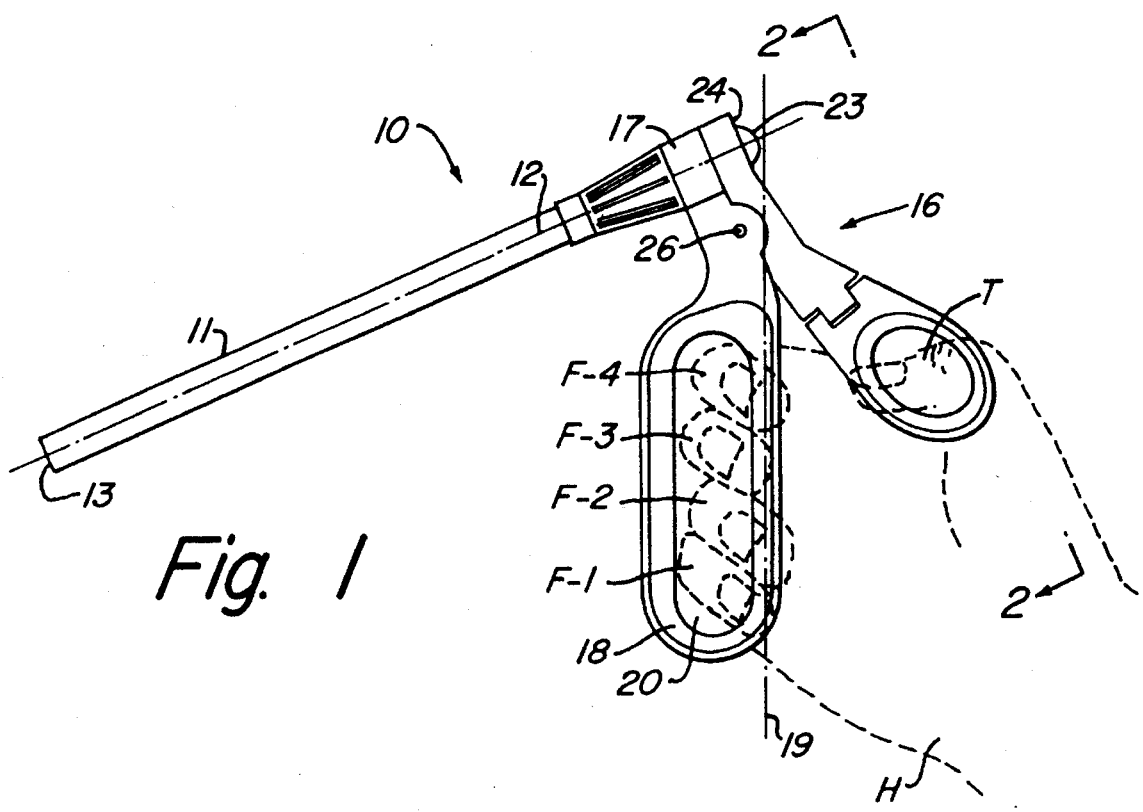
FIG. 1 is a side external view of the endoscopic surgical instrument of the present invention being positioned around the thumb and fingers of a surgeon or other operator, as shown in dotted line.
Figure 2:
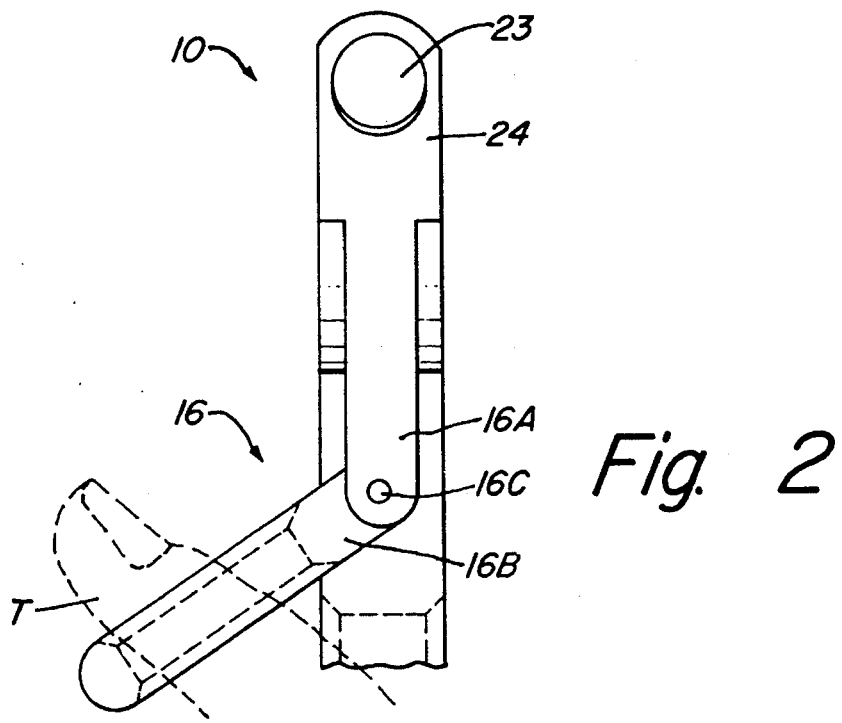
FIG. 2 is a sectional view taken along line 2—2 of FIG. 1 illustrating the pivoting movement of a portion of the manipulator means by means of the thumb of the surgeon or operator.
Figure 6:
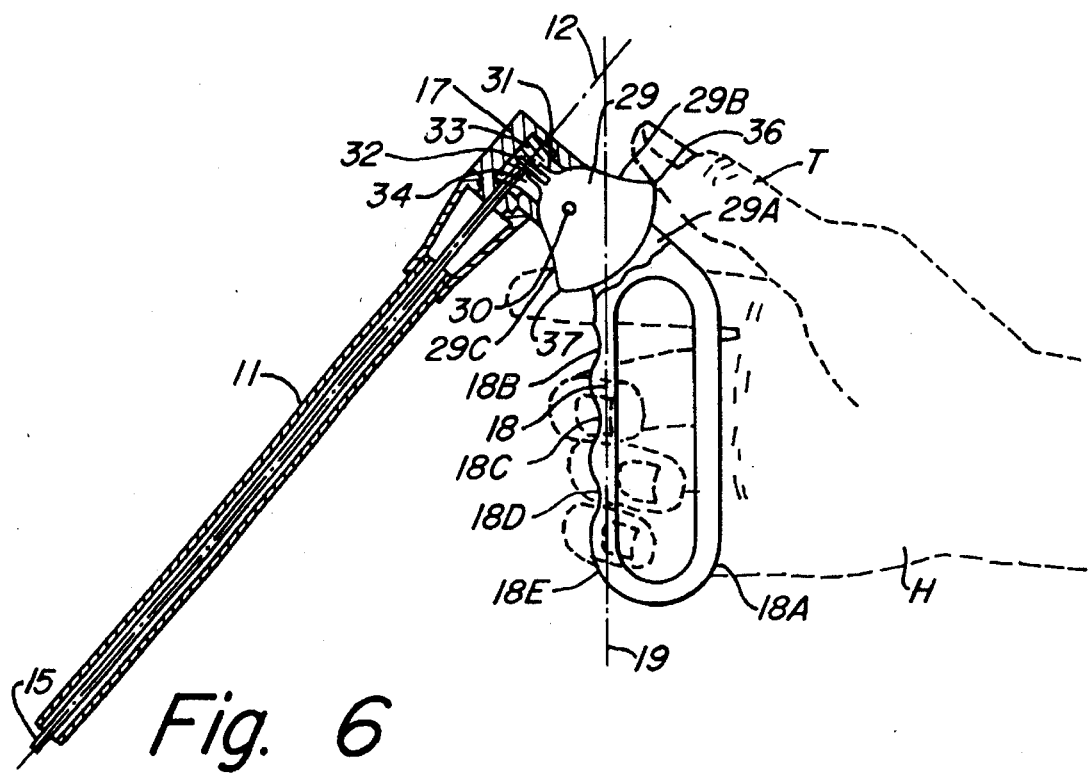
FIG. 6 is a partial longitudinal sectional and exterior view of an alternate embodiment of the present invention which includes a thumb-manipulatable biased pivot member for reciprocation of the instrument body relative to the housing, the pivot being shown in neutral position.
Figure 7:
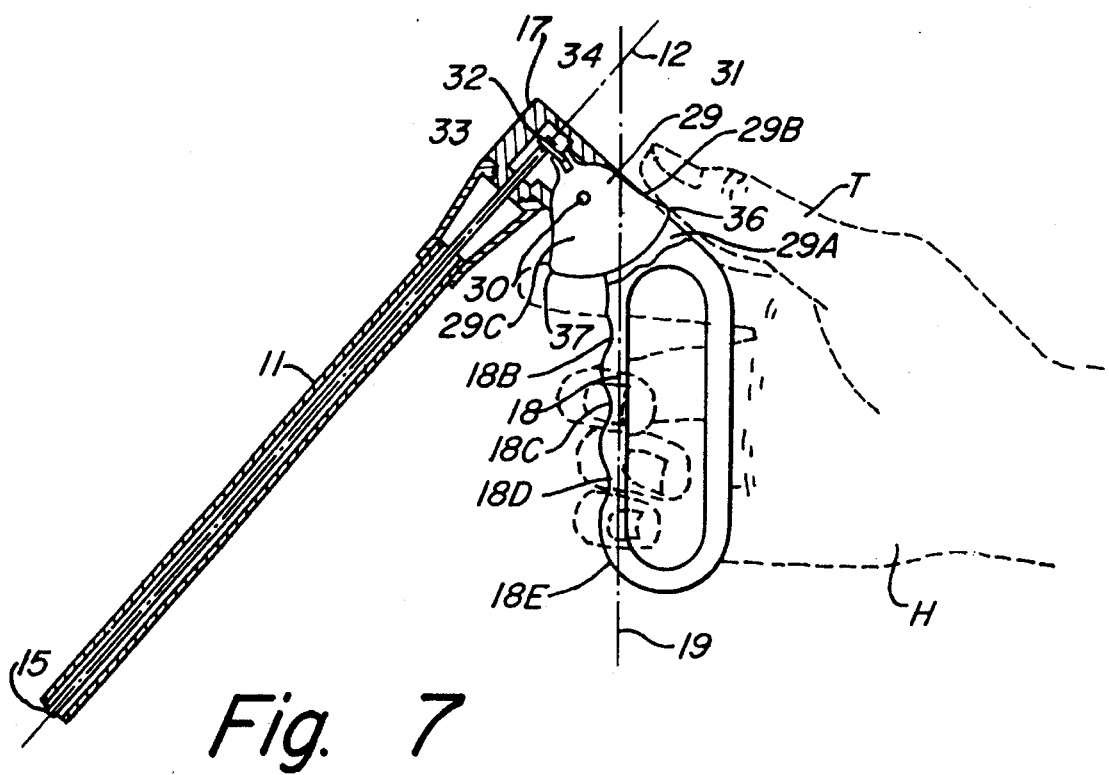
FIG. 7 is a view similar to that shown in FIG. 6 with the pivot moved from neutral position to a first, or retracting position.

Now, with particular first reference to FIGS. 1 and 3, there is shown an endoscopic surgical instrument 10 having an elongated outer cylindrical housing member 11. The housing member 11 has an end, preferably open, 13, which is first introduced through an incision (not shown) made through a body wall or cavity during endoscopic surgery. The housing 11 has a central longitudinal axis 12.

The elongated housing 11 interiorly contains an instrument body 14 which, as shown in FIG. 3, is concentrically disposed in the housing 11. The body 14 has an end 15 which, typically, may form or have secured or defined thereon a forceps assembly, needle, or other surgical instrument which is to be carried into the area of surgery on the instrument 10 and activated thereby.

Also, as shown in FIG. 3, the housing 11 includes as a portion thereof, a rotatable means or housing portion 22 which is rotatably secured relative to the control means 17, as discussed in more detail below.

The instrument body 14 is secured within the housing 11 by means of a button 23 interfacing a surface 24 of a member 16a of a manipulator means 16.

The control means 17 consist of a gripping means 18 and is operatively associated with a manipulator means 16 which is secured to the control means 17 by means of a pivot pin 26, such that the manipulator means 16 may pivot in relation to the control means 17 for relative telescopic movements between the instrument body 14 and housing 11.

The manipulator means 16, as particularly shown in FIGS. 1, 2, 3 and 4, includes a first member 16a which is secured to the control means 17 by means of the pivot pin 26 and which is joined to a second member 16b by means of pivot joinder 16c. An opening 16d is provided in the second member 16b for receipt of the thumb T of the surgeon or operator. As particularly shown in FIG. 2, the pivot joinder 16c between the first member 16a and second member 16b permits the thumb T of the operator to rotate the second member 16b relative to the first member 16a through manipulation of the member 16b by movement of the thumb T, for ease of operation, and to assist in reducing stress and/or fatigue to the thumb, fingers, hand and/or wrist of the surgeon or other operator during the surgical procedure.

Now referring in particular to FIGS. 1 and 3, the gripping means 18 has a grip entry 20 rectangularly defined through the gripping means 18 for receipt of the fingers F1, F2, F3, and F4 of the hand H of the operator. The gripping means has a section 18a upon which the fingers F1 through F4 of the operator grasp the instrument 10 to thereby define a grip axis 19 on the gripping means 18. The joinder of the grip axis 19 and the central axis 12 of the housing 11 provides an acute angle between the gripping means 18 and the housing 11.

Now referring, in particular, to FIGS. 4 and 5, the housing 11 includes a rotatable means 22 for rotatably securing the housing relative to the control means 17 for correct orientation during, prior to, or subsequent to, surgery. The rotatable means 22 has a series of laterally extending, outwardly protruding rib elements 28 (FIG. 4) for ease of grasp by the hand H of the operator when it is desired to rotate the housing 11.

The rotatable means 22 may be provided in a number of forms, such as provision of a groove interiorally and circumferentially defined around the rotatable means 22 at the outermost end thereof which receives a circularly extending doughnut-like ring on the control means 17.

Alternatively, as shown in FIG. 5, threads 27 may be provided between the interior of the rotatable means 22 and the control means 17 which may be selectively rotated for orientation of the housing 11 relative to the instrument body 14 during surgery.

An opening 25 is provided within the control means 17 and the manipulator means 16 for receipt of one end of the instrument body 14.

Now referring to FIGS. 6, 7, 8 and 9, there is shown an alternate embodiment of the instrument 10 in which a pivot 29 is provided on the gripping means 18. Additionally, FIGS. 6, 7, 8 and 9 show an alternate design of the gripping means 18, wherein the fingers F2, F3 and F4 are respectively received within valleys 18b, 18c and 18d in a forwardly-facing grip handle portion 18e. In this alternative design, the grip axis 19 is defined through the member 18e, because of the receipt of the fingers thereon, as opposed to receipt through the grip entry 20 such that the axis 19 would be otherwise defined on section 18a.

The pivot 29 is provided through an opening 29a within the control means 17, such that the pivot 29 takes the place of the manipulator means 16, as shown in FIGS. 1, 2, 3, 4 and 5. The pivot 29 is joined to the instrument body 14 through a "T" 32 defined on the instrument body 14 which is, in turn, received through a companion groove 31 on the pivot 29.

First and second spring members 33, 34 are provided within the interior of the control means 17 and are separated by a spring separator or block 35. The thumb T of the hand H of the surgeon or other operator may be applied to the smooth surface 29b of the pivot 29 to move the pivot from a neutral position to bias the spring 34 and reduce the bias on the spring 33 to move the instrument body 14 relative to the housing 11 from, for example, a neutral position to a retracted position.

Figure 8:
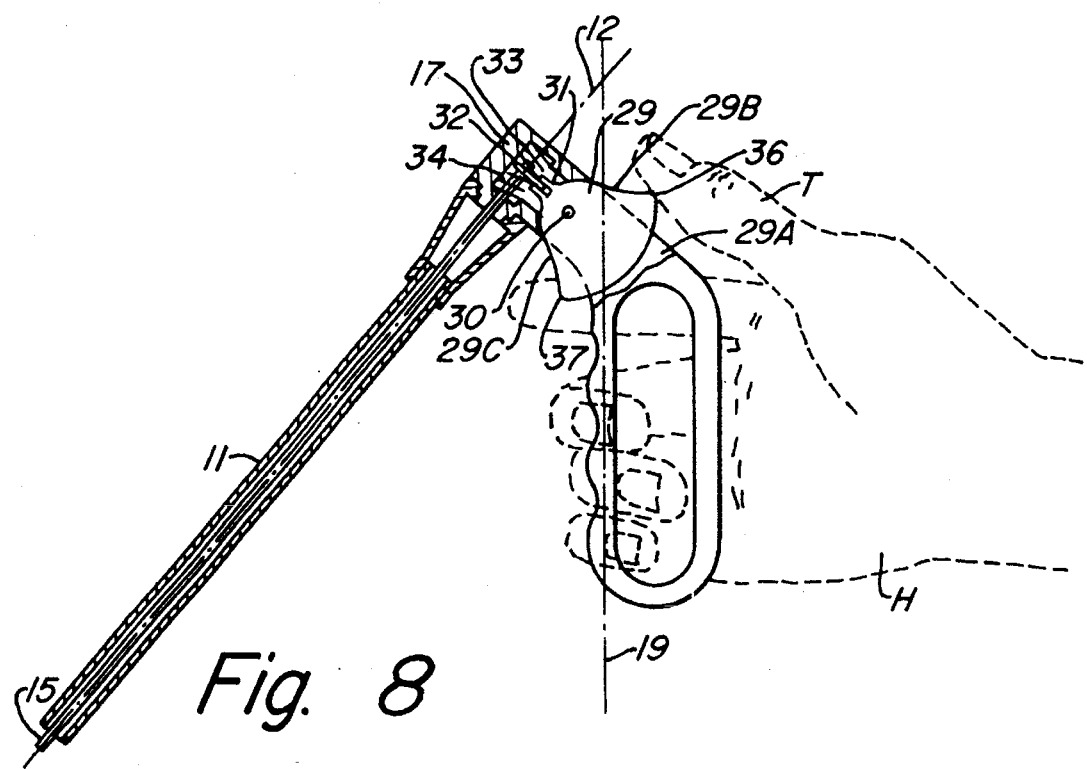
FIG. 8 is a view similar to that shown in FIGS. 6 and 7 with the pivot being illustrated in neutral position and prior to activation to a second position by means of a finger of the surgeon or other operator.
Figure 9:
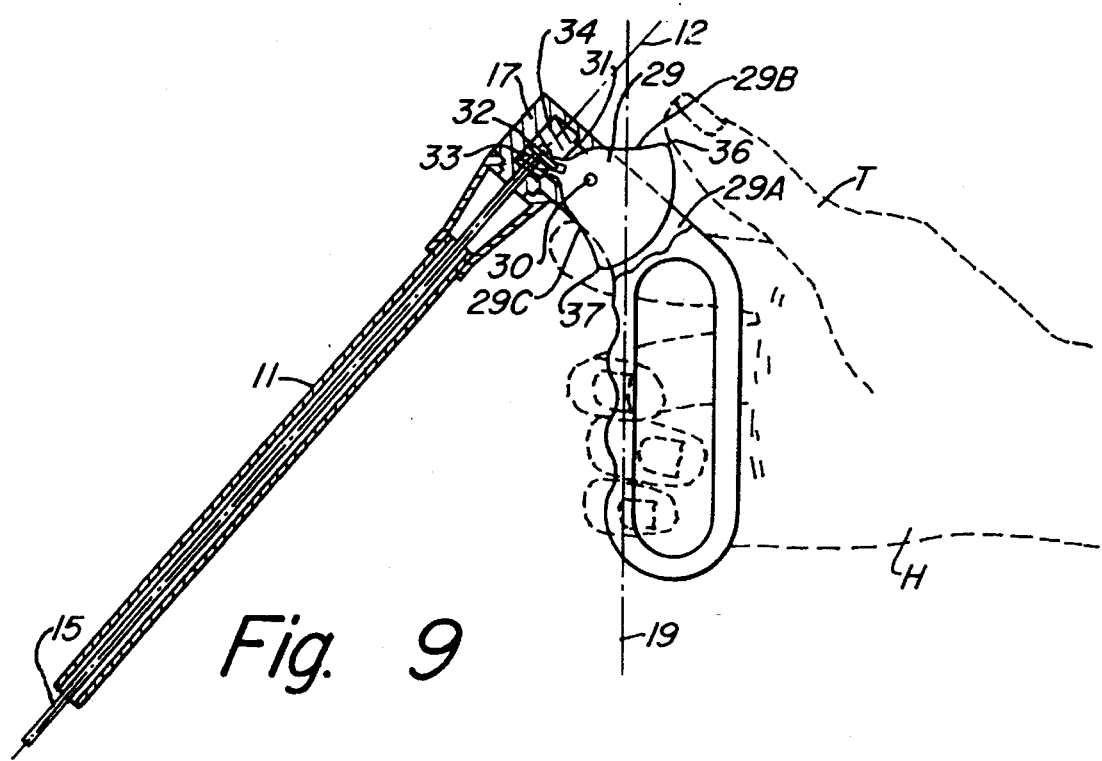
FIG. 9 is a view similar to that shown in FIGS. 6, 7 and 8, but illustrating the positioning of the pivot by a finger of the operator subsequent to the neutral position of FIG. 8, and illustrating the position of the pivot and instrument upon activation of the pivot to move the body relative to the housing to the second position.

Alternatively, the finger F4 of the surgeon or other operator may be applied, initially or subsequently, to a companion opposing face or surface 29c on the pivot 29, as shown in FIGS. 8 and 9, to apply a bias on the spring 33 and remove a bias on the spring 34 to move the instrument body 14 from a neutral position relative to the housing 11 to an expanded position.

Upon removal of the finger F4 from the surface 29c of the pivot 29, the increased bias in the spring 33 will cause the instrument body 14 and the pivot 29 to be moved relative to the housing 11 to a neutral point which is defined by encountering the normal bias defined through the second spring 34.

Although the invention has been described in terms of specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit from the invention.

What is claimed and desired to be secured by Letters Patent is:

1. An endoscopic surgical instrument manually manipulatable by a human surgical operator, comprising:

an elongated surgical instrument housing having a central axis and having a first end for introduction into the human body through a surgical incision;

a surgical instrument body disposed with said housing movable relative to said housing and having one end extendable through the first end of said instrument housing;

a manipulator movably coupled to said housing and operatively connected to said instrument body for controlling relative movements between said housing and said body, said manipulator including first and second members, the first of said members being secured to said grip and said body, the second of said members having an opening therethrough for receipt of the thumb or other finger of the surgical operator, the first and second members being pivotally joined at a point whereby the second member may be pivotally manipulated relative to said first member and transversely to said central axis; and a grip rigidly joined to said housing.

2. The surgical instrument of claim 1 wherein said grip having an entry through which the fingers of the surgical operator penetrate to encircle at least a portion of the grip for engagement thereof.

3. The surgical instrument of claim 1 further comprising means rotatably securing said housing to said grip whereby said housing at the first end may be selectively rotated up to 360 degrees around said instrument body.

4. An endoscopic surgical instrument manually manipulatable by a human surgical operator, comprising:

an elongated surgical instrument housing having a central axis and a first end for introduction into the human body through a surgical incision;

a surgical instrument body disposed within said housing movable relative to said housing and having one end extendable through the first end of said instrument housing;

a grip rigidly joined to said housing; and a manipulator movably coupled to said housing and operatively connected to said instrument body for controlling relative movements between said housing and said body, said manipulator including first and second members, the first member being secured to said grip and said body, and the second of said members having an opening therethrough for receipt of the thumb or other fingers of the surgical operator, the first and second members being pivotally joined at a point whereby the second of said members may be pivotally manipulated relative to said first member and transversely to said central axis.

5. The surgical instrument of claim 4 further comprising means rotatably securing said housing to said grip whereby said housing at the first end may be selectively rotated up to 360 degrees around said instrument body.

6. An endoscopic surgical instrument manually manipulatable by a human surgical operator, comprising:

an elongated surgical instrument housing having a central axis and a first end for introduction into the human body through a surgical incision;

a surgical instrument body disposed within said housing movable relative to said housing and having one end extendable through the first end of said instrument housing;

a grip rigidly joined to said housing;

a finger activatable pivot pivotally coupled to the housing and operatively connected to the instrument body, said pivot being disposed in a slot in the housing wherein a forward surface is exposed forward of said grip and an opposing rearward surface is exposed rearward of said grip;

a biasing member coupled between said pivot and said housing for maintaining said pivot in a neutral position intermediate a forward position and a rearward position, wherein said pivot is movable by a finger of said operator engaging said rearward surface from said neutral position to said forward position, and said pivot is movable by another finger of said operator engaging said forward surface from said neutral position to said rearward position, said movement of said pivot causing said body to move relative to said housing; and means rotatably securing said housing to said grip whereby said housing at the first end may be selectively rotated up to 360 degrees around said instrument body.

7. An endoscopic surgical instrument manually manipulatable by a human surgical operator, comprising:

an elongated surgical instrument housing having a first end for introduction into the human body through a surgical incision;

a surgical instrument body disposed within said housing movable relative to said housing and having one end extendable through the first end of said instrument housing;

a grip rigidly joined to said housing; and a finger activatable pivot coupled to said housing and operatively connected to said instrument body, said pivot being disposed in a slot in the housing wherein a forward surface is exposed forward of said grip and an opposing rearward surface is exposed rearward of said grip; and a biasing member coupled between said pivot and said housing for maintaining said pivot in a neutral position intermediate a forward position and a rearward position, wherein said pivot is movable by a finger of said operator engaging said rearward surface from said neutral position to said forward position, and said pivot is movable by another finger of said operator engaging said forward surface from said neutral position to said rearward position, movement of said pivot causing said instrument body to move relative to said housing.

8. An endoscopic surgical instrument manually manipulatable by a human surgical operator, comprising:

an elongated surgical instrument housing having a central axis and having a first end for introduction into the human body through a surgical incision;

a surgical instrument body disposed within said housing;

a grip rigidly joined to said housing and having a grip axis that intersects the central axis of the housing to define an acute angle between the grip axis and the housing; and a manipulator movably coupled to said housing and operatively connected to said instrument body for controlling relative movements between said housing and said body, said manipulator including first and second members, the first member being secured to said grip and said body, and the second of said members having an opening therethrough for receipt of the thumb or other fingers of the surgical operator, the first and second members being pivotally joined at a point whereby the second of said members may be pivotally manipulated relative to said first member and transversely to said central axis.

9. The endoscopic surgical instrument of claim 8, wherein said grip is provided with an entry through which the fingers of the surgical operator penetrate to encircle at least a portion of the gripping means for engagement thereof.

10. An endoscopic instrument manually manipulatable by a human surgical operator, comprising:

an elongated surgical instrument housing having a central axis and having a first end for introduction into the human body through a surgical incision;

a surgical instrument body disposed within said housing and movable relative to said housing;

a grip rigidly joined to said housing and having a grip axis that intersects the central axis of the housing to define an acute angle between the grip axis and the housing; and a finger activatable pivot operatively connected to said instrument body and pivotally coupled to said grip, said pivot being disposed in a slot in the housing wherein a forward surface is exposed forward of said grip and an opposing rearward surface is exposed rearward of said grip; and a biasing member coupled between said pivot and said housing for maintaining said pivot in a neutral position intermediate a forward position and a rearward position, wherein said pivot is movable by a finger of said operator engaging said rearward surface from said neutral position to said forward position, an said pivot is movable by another finger of said operator engaging said forward surface from said neutral position to said rearward position, said movement of said pivot causing said instrument body to move relative to said housing.

11. The endoscopic surgical instrument of claim 10, wherein said grip is provided with an entry through which the fingers of the surgical operator penetrate to encircle at least a portion of the gripping means for engagement thereof.

* * * * *